United States Patent [19]

Randolph et al.

[11] Patent Number: 5,659,096
[45] Date of Patent: Aug. 19, 1997

[54] COMBINATION OF OLEFIN OLIGOMERIZATION AND PARAFFIN ALKYLATION

[75] Inventors: Bruce B. Randolph; Marvin M. Johnson, both of Bartlesville, Okla.

[73] Assignee: Phillips Petroleum Company, Bartlesville, Okla.

[21] Appl. No.: 462,250

[22] Filed: Jun. 5, 1995

[51] Int. Cl.⁶ .................................................. C07C 2/00
[52] U.S. Cl. ........................... 585/332; 585/529; 585/712; 585/719; 585/721; 585/723
[58] Field of Search ..................... 585/721, 723, 585/712, 719, 332, 529

[56] References Cited

U.S. PATENT DOCUMENTS

| | | |
|---|---|---|
| 3,449,459 | 6/1969 | Asfazdourian et al. |
| 3,662,020 | 5/1972 | Hemminger et al. |
| 3,799,263 | 3/1974 | Prillieux et al. ............ 166/275 |
| 3,932,553 | 1/1976 | Robert . |
| 4,029,601 | 6/1977 | Wiese . |
| 4,234,750 | 11/1980 | Mikulicz ................... 585/332 |
| 4,286,110 | 8/1981 | Chapman ................... 585/719 |
| 4,675,463 | 6/1987 | Glivicky et al. ........... 585/514 |
| 5,081,086 | 1/1992 | Wilcher et al. ............ 502/81 |

*Primary Examiner*—Glenn Caldarola
*Assistant Examiner*—Elizabeth D. Wood
*Attorney, Agent, or Firm*—Charles W. Stewart

[57] ABSTRACT

In a process for alkylating $C_4$–$C_{18}$ alkenes in the presence of an acid catalyst, propylene is separated from the alkenes feed, the propylene is oligomerized to oligomers containing maily propylene tetramers, and the propylene oligomers are then combined with the remainder of the alkene feed before the alkylation reaction is carried out.

12 Claims, No Drawings

COMBINATION OF OLEFIN OLIGOMERIZATION AND PARAFFIN ALKYLATION

BACKGROUND OF THE INVENTION

The present invention relates to a process for alkylating paraffins with monoolefins. In another aspect, this invention relates to an alkylation process where one of the feed monoolefins is first oligomerized before its use as an alkylating agent.

Monoolefin (alkene) feedstocks for the alkylation of paraffins (alkanes) frequently contain propylene. Even though propylene is an effective alkylation agent, its use has undesirable effects: formation of propane Coy hydrogen transfer) as a byproduct which places a heavy load on a lights distillation column (called depropanizer), and high amounts of isopentane (which is relatively volatile and is not a good blending component for motor fuels) in produced alkylates.

The prior art teaches to take propylene out of an olefin feedstock (for paraffin alkylation), to dimerize the propylene, and to recombine the formed propylene dimers with the olefin feedstock, as is described in U.S. Pat. No. 3,662,020. The present invention is an improvement over this prior art process.

SUMMARY OF THE INVENTION

It is an object of this invention to alkylate a paraffin (alkane) feed stream with a monoolefin (alkene) feed stream to produce an alkylate of relatively low Reid vapor pressure. It is another object of this invention to oligomerize propylene contained in the monoolefin feed stream before the paraffin alkylation is carried out. Other objects and advantages become apparent from the detailed description and the appended claims.

According to this invention, in an alkylation process which comprises contacting (a) a first feed comprising at least one alkane containing 4–18 carbon atoms and (b) a second feed comprising propylene and at least one feed alkene containing 4–18 carbon atoms per molecule substantially simultaneously with (c) an acid-containing catalyst at effective alkylation conditions, so as to produce an alkylation product comprising at least one alkane containing more carbon atoms per molecule than said at least one feed alkane, the improvement comprises: (i) substantially separating propylene from said second feed, (ii) introducing the separated propylene into an oligomerization reaction zone wherein said propylene is catalytically oligomerized to an oligomerization product consisting essentially of propylene tetramers as major components and propylene trimers as minor compounds, and (iii) combining said oligomerization product with said second feed before said contacting with said acid-containing catalyst.

The preferred acid-containing alkylation catalyst is hydrofluoric acid. Preferably, the catalyst for the oligomerization of propylene is phosphoric acid on kieselguhr.

Detailed Description of the Invention

The basic process for alkylating $C_4$–$C_{18}$ alkanes (which may be linear or branched) with propylene and $C_4$–$C_{18}$ alkenes (which may be linear or branched) in the presence of an acid catalyst is well known and has been described in numerous patents. Preferably, both the feed alkane(s) and the feed alkene(s) contain about 4–12 C atoms per molecule. Examples of particularly suitable feed alkanes include (but are not limited to) isobutane, isopentanes, isohexanes, isoheptanes, isooctanes, and the like, and mixtures thereof. Non-limiting examples of particularly suitable feed alkenes (besides propylene) include but are not limited to n-butene-1, n-butene-2, isobutylene, linear and branched pentenes (amylenes), linear and branched hexenes, linear and branched heptenes, linear and branches octenes and the like, and mixtures thereof. Generally, the propylene content in the second feed is about 0.5–95 weight-%, preferably about 5–20 weight-%.

Any suitable acid catalyst can be employed in this reaction. Suitable catalysts include (but are not limited to) hydrofluoric acid (presently preferred), mixtures of HF and a sulfolane compound, sulfuric acid, sulfonic acids such as trifluoromethanesulfonic acid (with or without an inorganic support material, such as silica or other well known support materials for $CF_3SO_3H$ which are disclosed in the patent literature), zeolites, Friedel-Crafts compounds such as $AlCl_3$ and $BF_3$, heteropolyacids such as tungstophosphoric acids and molybdophosphoric acids, and alkali metal salts of these heteropolyacids. In the preferred embodiment of this invention, anhydrous HF is used as the catalyst. Typical preferred alkylation conditions include a temperature range of about 80° to about 120° F. (more preferably about 90°–110° F.), a pressure in the range of about 60 to about 200 psig (more preferably about 90–120 psig), and an alkane to alkene molar ratio of about 5:1 to about 20:1 (more preferably about 8:1 to about 15:1).

Improvement step (i), i.e., the separation of propylene from an alkene feed, can be carried out in any suitable manner. Generally, this separation is carried out in a distillation column by fractional distillation at a temperature low enough and a pressure high enough to have the alkene feed present substantially in the liquid phase. Suitable temperature/pressure conditions for step (i) include a distillation column pressure of about 250–300 psig, a column overhead temperature (in the top region of the column) of about 100°–130° F. and a column bottom temperature (in the bottom region of the column) of about 200°–250° F. Any effective distillation column containing internal packing material (such as Raschig rings or saddles, trays or bubble caps) can be used for the substantial separation of propylene from the feed alkenes ($C_4$–$C_{12}$ alkenes).

Improvement step (ii), i.e., the conversion of propylene to an oligomerization product comprising primarily propylene tetramers (i.e., dodecenes), can be carried out in any suitable, effective manner employing any effective oligomerization catalyst. Examples of such catalysts include (but are not limited to), Friedel-Crafts compounds (such as BF3, $AlCl_3$), cobalt oxide on carbon, sulfuric acid, and phosphoric acid (with or without a solid support material). These catalysts are disclosed in U.S. Pat. Nos. 3,449,459; 3,932,553; 4,029,601 and 4,675,463. A preferred catalyst system comprises phosphoric acid on kieselguhr. Temperature/pressure conditions for this oligomerization step vary widely depending on which specific catalyst system is used. In the case of a phosphoric acid on kieselguhr catalyst, the oligomerization temperature generally is about 150°–230° C. (about 302°–446° F.) and the pressure generally is about 4.1–8.2 MPa (about 595–1190 psi). The preferred oligomerization product contains in excess of about 50 weight-% alkenes containing about 11–13 (more preferably about 12) carbon atoms per molecule, preferably about 70–99.9 weight-% $C_{11}$–$C_{13}$ alkenes. The remainder (less than about 50 weight-%; preferably about 0.1–30 weight-%) consists essentially of $C_8$–$C_{10}$ alkenes (more preferably alkenes containing about 9 C atoms per molecule). Propylene dimers such as methylpentenes and dimethylbutenes are substantially absent from the oligomerization product.

Improvement step (iii) can be carried out in any suitable manner. Generally, the entire reaction product of step (ii) is combined with the original alkene feed which remained after propylene had been removed therefrom in step (i). Optionally, the oligomerization product of step (ii) undergoes a refractive distillation separation so as to remove therefrom undesirable oligomerization by-products, such as small mounts of propylene dimers and oil (high molecular weight products) before said oligomerization product is combined with the alkene feed in step (iii).

The following example is presented to further illustrate preferred embodiments of this invention and not to be construed as unduly limiting the scope of the invention.

EXAMPLE

A continuous reactor system was used for the alkylation reactions under continuous conditions. The alkylation reactor consisted of a 2 ft. long section of Monel schedule 40 pipe (volume: 308 mL) which was connected, via ¼" Monel tubing, to a Monel sight gauge (volume: 704 mL) which was used as a settling vessel ("settler"). The reactor system was charged with the desired amount of anhydrous HF (about 650–700 grams). The acid was circulated through the reactor and settler by means of a small gear pump. The desired feed olefin (either propylene or propylene dimers or propylene tetramers) was blended with isobutane to attain the desired isobutane/olefin weight ratio (about 9:1 to 11:1). The blended feed was then pumped into the reactor (rate: 300 mL/hr) through a feed nozzle (0.01" orifice) to provide high dispersion. The acid settled to the bottom of the sight gauge, was passed through a heat exchanger and returned to the reactor. Reactor temperatures of 95°–105° F. and reaction pressure of about 100 psig were employed in all rims. Acid samples were withdrawn at 24 hour intervals, and makeup HF was added to keep the catalyst activity at the desired level.

The hydrocarbon product (settler effluent) was drawn out of the top of the settler and passed over beds packed with ¼ alumina beads to remove small amounts of dissolved HF present in the settler effluent. The HF-free settler effluent was then passed through a back-pressure regulator, and the volatile materials were flashed at ~68° F. and 15 psig. The liquid product was collected in a 2 gallon receiver and drained at desired time intervals into a sample bomb for gas chromatographic (GC) analysis. Samples of the flashed off-gas were also taken for GC analysis. Average liquid product compositions and pertinent properties are summarized in TABLE 1.

TABLE 1

| Run | Feed Olefin | Liquid Alkylation Product Composition (Weight %)[2] | | | | | | Product Reid Vapor Pressure[4] | Product Octane No.[5] |
|---|---|---|---|---|---|---|---|---|---|
| | | Light[3] | Isopentane | $C_6$ Alkanes | $C_7$ Alkanes | $C_8$ Alkanes | $C_9^+$ Alkanes | | |
| 1 (Control) | Propylene | 1.8 | 4.0 | 4.6 | 29.4 | 40.5 | 19.4 | 3.3 | 88.7 |
| 2 (Control) | Methylpentenes | 1.5 | 7.2 | 13.2 | 2.4 | 37.4 | 38.3 | 4.0 | 85.7 |
| 3 (Control) | Dimethylbutenes | 0.7 | 2.9 | 19.0 | 2.8 | 55.4 | 19.0 | 3.6 | 92.3 |
| 4 (Invention) | Propylene Tetramers[1] | 1.0 | 1.0 | 1.1 | 3.3 | 36.3 | 57.1 | 0.9 | 85.2 |

[1] commercially available from Exxon Chemical Company, Houston, Texas, containing about 99 weight % $C_{11}$–$C_{13}$ monoolefins and about 1 weight % $C_8$–$C_{10}$ monoolefins; essentially no hexanes and heptanes were present.
[2] based on product excluding unconverted isobutane.
[3] $C_2$–$C_4$ alkanes and organic fluorides.
[4] calculated; given in psi units at 100° F.
[5] calculated; (Research Octane No. + Motor Octane) No./2.

Test data in Table I clearly show that the invention run employing propylene tetramers as the olefin feed produced a liquid alkylate which contained less of the volatile isopentane and had a lower vapor pressure than control runs 1–3 employing propylene or propylene dimers (methylpentanes or dimethylbutenes) as feeds. In addition, the alkylate of invention run 4 contained more $C_9+$ alkanes, which are useful as blending components for specialty solvents (such as "Soltrol", marketed by Phillips Chemical Company, Bartlesville, Okla.).

A more detailed analysis (not described in detail herein) of each produced $C_8$ alkane fraction (useful as blending components for motor fuels such as gasoline) revealed that the weight ratio of highly branched trimethylpentanes (TMP) to less branched dimethylhexanes (DMH) was considerably higher for invention run 4 (about 5.3:1) than for the control rims (about 3.8:1 in runs 1 and 2; about 4.3:1 in run 3). A high TMP/DMH ratio is desirable for gasoline blending stocks (because TMP has a higher octane number than DMH).

Reasonable variations, modifications and adaptations for various conditions which will be apparent to those skilled in the art, can be made within the scope of the disclosure and the appended claims without departing from the scope of this invention.

That which is claimed:

1. In an alkylation process which comprises contacting (a) a first feed comprising at least one feed alkane containing 4–18 carbon atoms per molecule and (b) a second feed comprising propylene and at least one feed alkene containing 4–18 carbon atoms per molecule substantially simultaneously with (c) an acid-containing catalyst at effective alkylation conditions, so as to produce an alkylation product comprising at least one alkane containing more carbon atoms per molecule than said at least one feed alkane, the improvement which comprises:

(i) separating propylene from said second feed,
   (ii) introducing the separated propylene into an oligomerization reaction zone wherein said propylene is catalytically oligomerized to an oligomerization product consisting essentially of alkenes containing 11–13 carbon atoms per molecule as major components and alkenes containing 8–10 carbon atoms per molecule as minor components, and (iii) combining said oligomerization product with said second feed before said contacting with said acid-containing catalyst.

2. A process in accordance with claim 1, wherein said second feed contains about 0.5–95 weight-% propylene.

3. A process in accordance with claim 1 wherein said at least one feed alkane contains about 4–12 carbon atoms per molecule and said at least one feed alkene contains 4–12 carbon atoms per molecule.

4. A process in accordance with claim 1, wherein said catalyst comprises hydrofluoric acid.

5. A process in accordance with claim 1, wherein said at least one feed alkane is selected from the group consisting of isobutane, isopentanes, isohexanes, isoheptanes, isooctanes and mixtures thereof; the at least one feed alkene is selected from the group consisting of n-butene-1, n-butene-2, isobutylene, linear pentenes, branched pentenes, linear hexenes, branched hexenes, linear heptenes, branched heptenes, linear octenes, branched octenes, and mixtures thereof; and said catalyst is anhydrous hydrofluoric acid.

6. A process in accordance with claim 5, wherein said effective alkylation conditions comprise a temperature of about 80°–120° F., a pressure of 60–200 psig, and an alkane to alkene ratio of about 5.1 to about 20:1.

7. A process in accordance with claim 1, wherein step (i) is carried out by fractional distillation employing a distillation column.

8. A process in accordance with claim 7, wherein the pressure in said distillation column is about 250–300 psig, the temperature in the top region of said distillation column is about 100°–130° F., and the temperature in the bottom region of said distillation column is about 200°–250° F.

9. A process in accordance with claim 1, wherein the catalyst employed in step (ii) is phosphoric acid on kieselguhr.

10. A process in accordance with claim 9, wherein step (ii) is carried out at a temperature of about 302°–446° F. and a pressure of about 595–1190 psi.

11. A process in accordance with claim 10, wherein the oligomerization product obtained in step (ii) comprises about 70–99.9 weight-% $C_{11}$–$C_{13}$ alkenes.

12. A process in accordance with claim 11, wherein propylene dimers are substantially absent from said oligomerization product.

* * * * *